United States Patent [19]

Hillel et al.

[11] Patent Number: 4,507,112
[45] Date of Patent: Mar. 26, 1985

[54] INFUSION MONITOR

[75] Inventors: Arie Hillel, Tel Aviv; Simcha Borovsky, Givatayim, both of Israel

[73] Assignee: IPCO Corporation, White Plains, N.Y.

[21] Appl. No.: 581,814

[22] Filed: Feb. 21, 1984

Related U.S. Application Data

[63] Continuation of Ser. No. 365,595, Apr. 5, 1982, abandoned.

[51] Int. Cl.³ ............................................... A61M 5/00
[52] U.S. Cl. .............................. 604/65; 128/DIG. 13; 222/63; 137/486
[58] Field of Search ............... 128/DIG. 13; 137/486, 137/487, 487.5; 222/14, 17, 20, 52, 53, 63; 604/19, 30, 65–67, 246–247, 250

[56] References Cited

U.S. PATENT DOCUMENTS

| 3,335,753 | 8/1967 | Kiser | 128/DIG. 13 |
| 3,563,090 | 2/1971 | Deltour | 128/DIG. 13 |
| 4,018,362 | 4/1977 | Ubaud | 222/55 |
| 4,237,878 | 12/1980 | Kobayashi et al. | 128/DIG. 13 |
| 4,321,461 | 3/1982 | Walls et al. | 604/65 X |

Primary Examiner—Edward M. Coven
Attorney, Agent, or Firm—Stoll, Wilkie, Previto & Hoffman

[57] ABSTRACT

An infusion monitor for feeding liquids to patients which is light weight so that it may be easily hung on a liquid dripper and which is provided with means for pre-setting the volume infused and the rate of infusion. Means are also provided for automatically varying the rate of infusion, for automatically cutting-off the infusion and for sounding an alarm to alert an attendant if any variation from pre-set limits occur.

81 Claims, 8 Drawing Figures

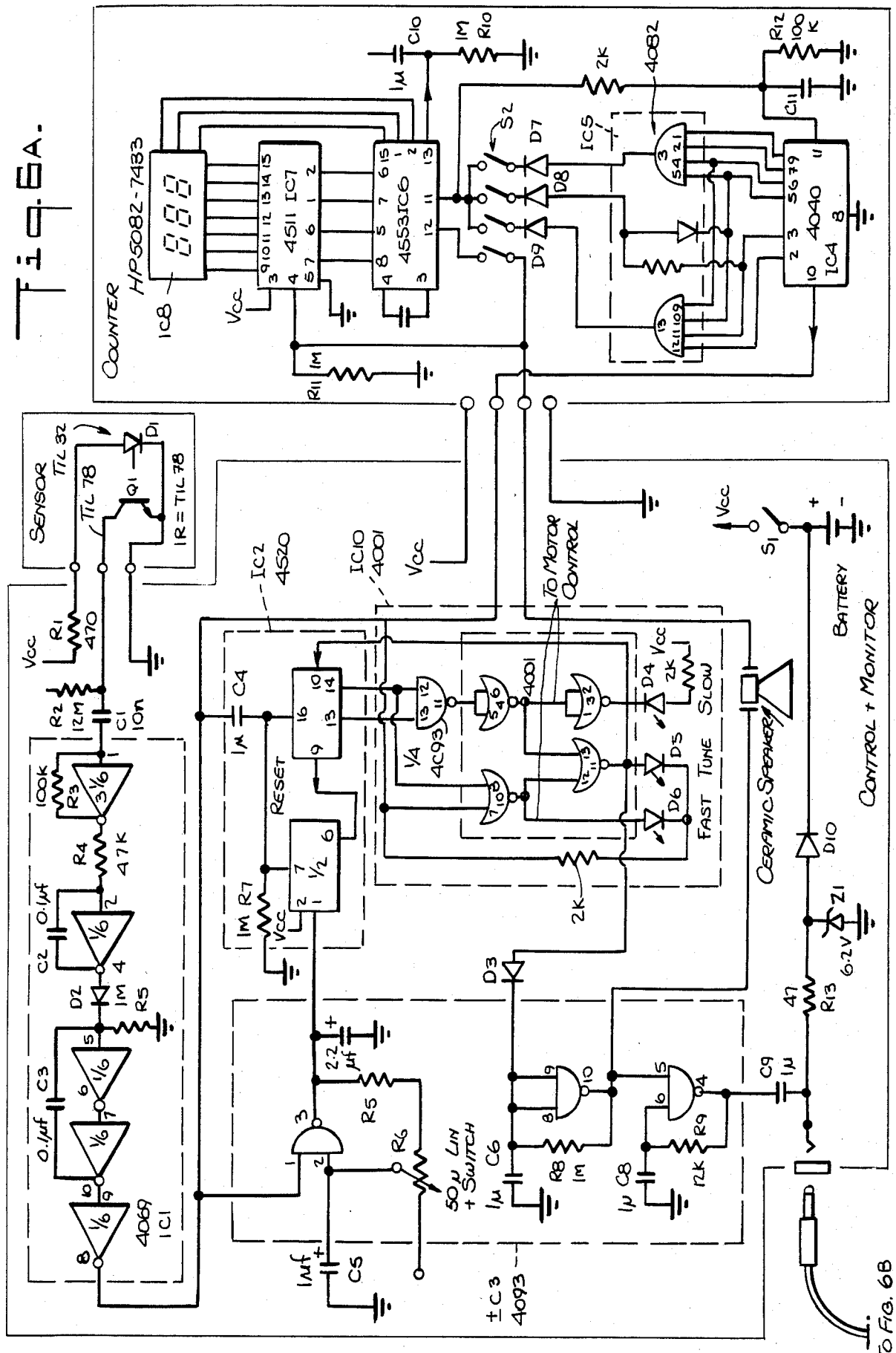

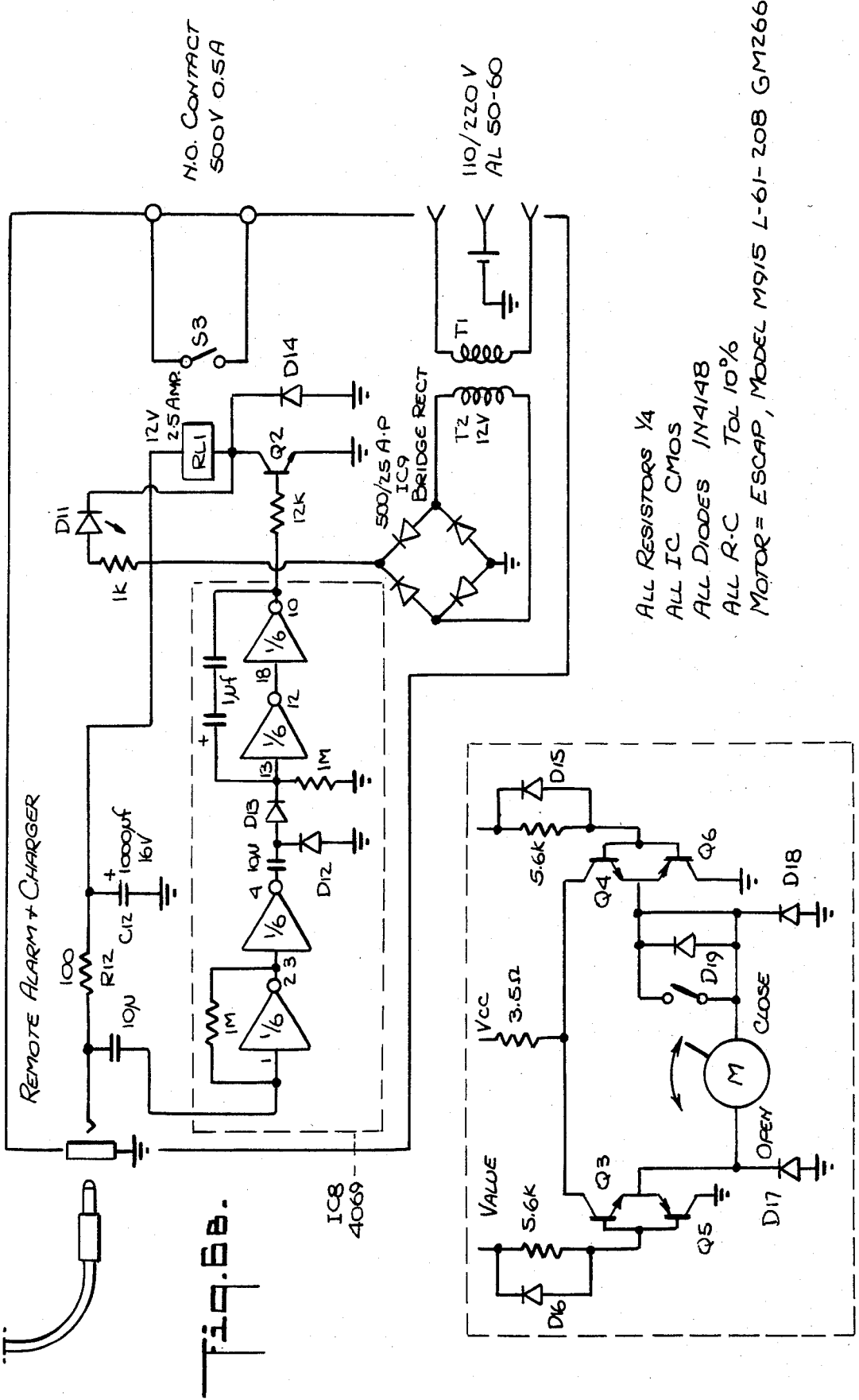

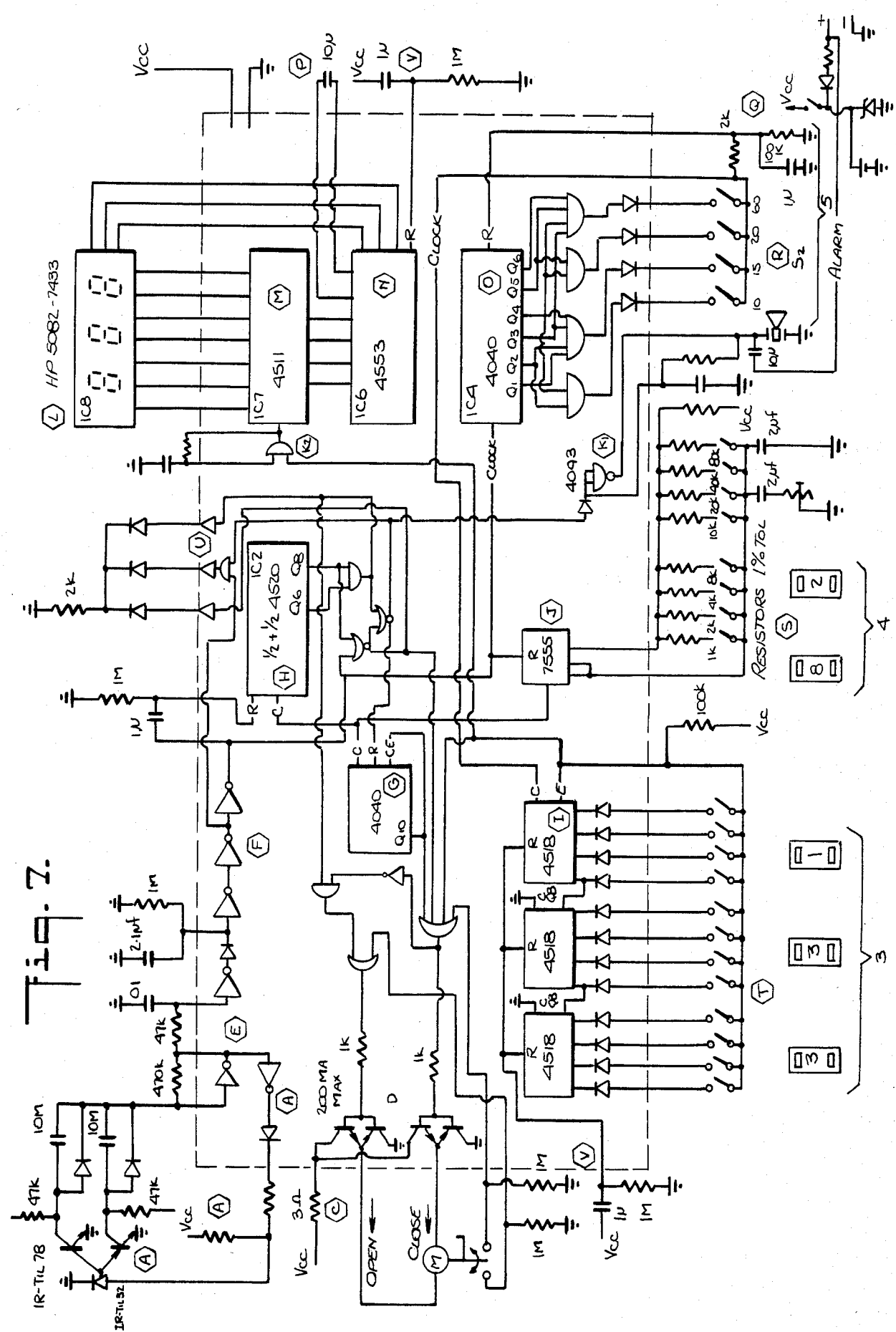

4,507,112

INFUSION MONITOR

RELATED APPLICATION

This application is a continuation of pending U.S. application Ser. No. 365,595 filed Apr. 5, 1982 now abandoned.

BACKGROUND OF THE INVENTION

Intravenous liquid infusion means for infusing patients with food, blood, drugs, and the like are used in numerous medical applications. Infusion monitors usually comprise a suitable reservoir for the solution to be infused which is connected to a dripper and from which extends a feed tube leading to an intravenous needle for injection at the venipuncture point of the patient. A tube clamp is normally placed along the feed tube to control the flow of the liquid being infused. The proper and reliable control of the rate and volume of infusing these liquids is essential to patient management and recovery. Proper infusion rates and volume may vary from a few cubic centimeters per hour to several cubic centimeters per minute. Hence, it is extremely important that the infusion rate and volume be accurately and continuously monitored and controlled.

Heretofore, the methods employed for monitoring and controlling the rate and volume of infusion have been time-consuming and of limited accuracy. Typically, an attendant sets the flow rate by counting the drops per minute from the reservoir. The rate is thus determined slowly, with difficulty and with little accuracy. Because of the heavy pressure on the attendant's time, there is usually little or no correction for any variations in the flow rate or for clearing of any blockage of the needle by clotting, etc. Such blockages can be dangerous to the patient if not readily noted and require time-consuming and painful needle replacement to re-establish flow. Similar difficulties arise when an empty bottle goes unnoticed.

In the prior art there are also provided infusion monitoring systems which monitor the amounts infused by using electro-optical sensing means. However, in such systems, the cartridge and sensing systems are quite complicated and are connected to the feeding assembly by complicated clamping means. This requires complex alignments of the optical sensing system and more complex monitoring devices.

SUMMARY OF THE INVENTION

The present invention avoids the above difficulties and has for one of its objects an improved infusion monitor which will automatically and continuously monitor and adjust the desired flow rate.

Another object of the present invention is the provision of an improved infusion monitor which is light and simple so that it may be hung directly from the dripper tube.

Another object of the present invention is the provision of an improved infusion monitor which will continuously indicate the amount of fluids infused into the patient.

Another object of the present invention is the provision of an improved infusion monitor which may be pre-set to shut-off the flow when the desired volume has been administered.

Another object of the present invention is the provision of an improved infusion monitor which is provided with warning devices which give signals at the patient's side and/or at the nurse's desk so that the attendant is alerted to any variation or stoppage of the pre-set infusion rate.

Other and further objects of the invention will be obvious upon an understanding of the illustrative embodiment about to be described, or will be indicated in the appended claims, and various advantages not referred to herein will occur to one skilled in the art upon employment of the invention in practice.

In accordance with the present invention, the instrument incorporates an electro-optical device which senses the drop rate and counts the number of drops infused. By pre-setting the unit to a predetermined number of drops per cubic centimeter, the number of drops counted by the optical system are translated to volume infused. This volume is continuously displayed on the instrument. A plastic feed tube leads from the dripper to the infusion needle and is attached to a squeezing mechanism operated by a motor in the instrument which automatically squeezes or releases the feed tube.

By pre-setting the desired drip rate, the squeezer will automatically squeeze or release the tube to tune the tube to allow the desired rate of drip only to be infused. The instrument may also be pre-set to the amount of liquid to be infused so that when the desired volume is reached, the instrument will command the squeezer to completely squeeze the tube and cut-off the flow. Fast and slow alarms, alerted by both light and sound, may be provided and a continuous alarm may also be provided to constantly alert the attendant when the flow is continuous, the bag is empty, or there is an electrical failure. This same information may be transmitted to the attendant's desk or to any other alert system.

The cartridge of the present invention is of such light weight that, together with the entire circuitry and the battery included therein, it may be hung from the dripper tube directly. Hence, the drops passing from the dripper tube may be sensed by the electro-optical sensing system of the present invention. This may be done without complicated clamping and sensing devices. dr

BRIEF DESCRIPTION OF THE DRAWINGS

A preferred embodiment of the invention has been chosen for purposes of illustration and description and is shown in the accompanying drawings forming a part of the specification, wherein:

FIGS. 6A and 6B are diagrammatic views showing the circuit in greater detail.

FIG. 7 is another diagrammatic view showing the circuit in still greater detail.

DETAILED DESCRIPTION OF THE INVENTION

Figure 1:
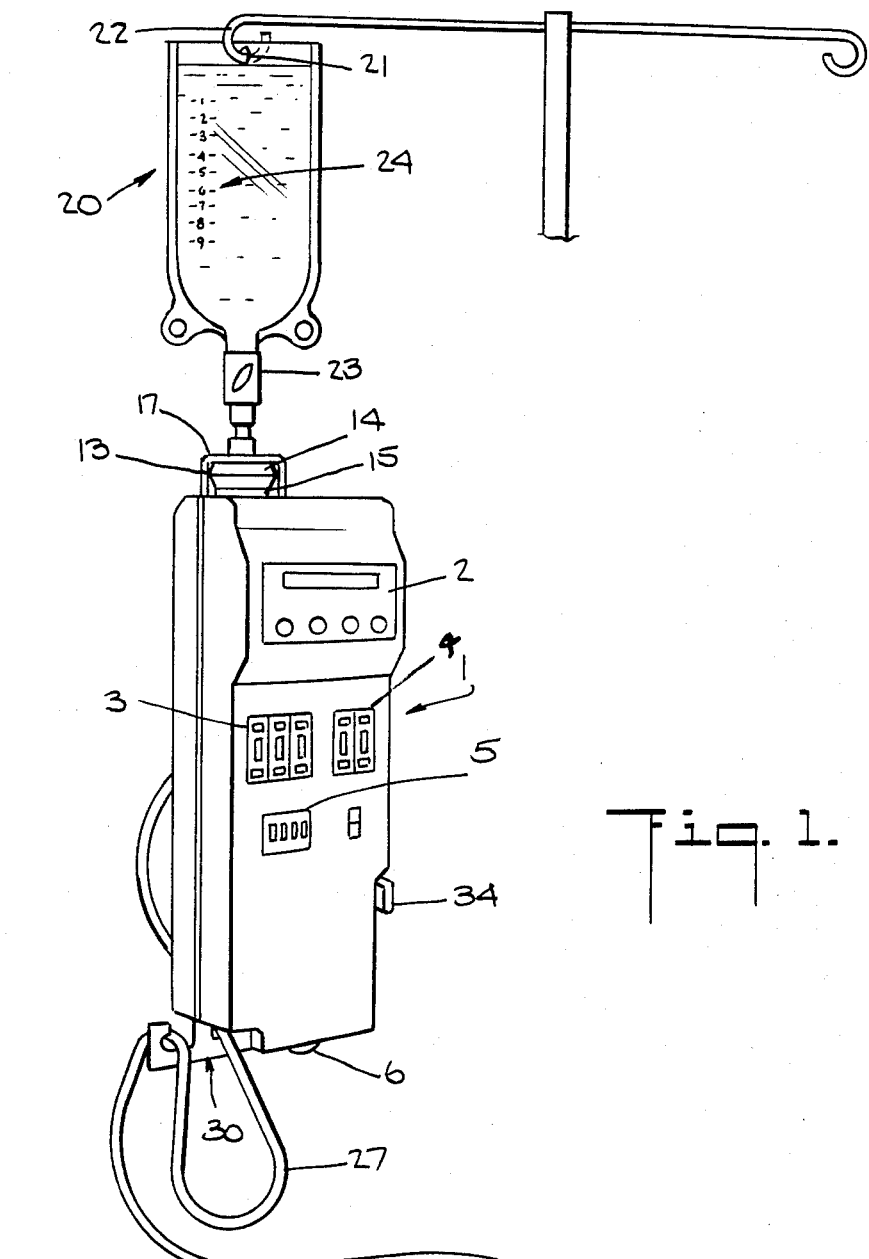
FIG. 1 is a perspective view showing the fusion monitor of the present invention in use and feeding a patient.
Figure 1:
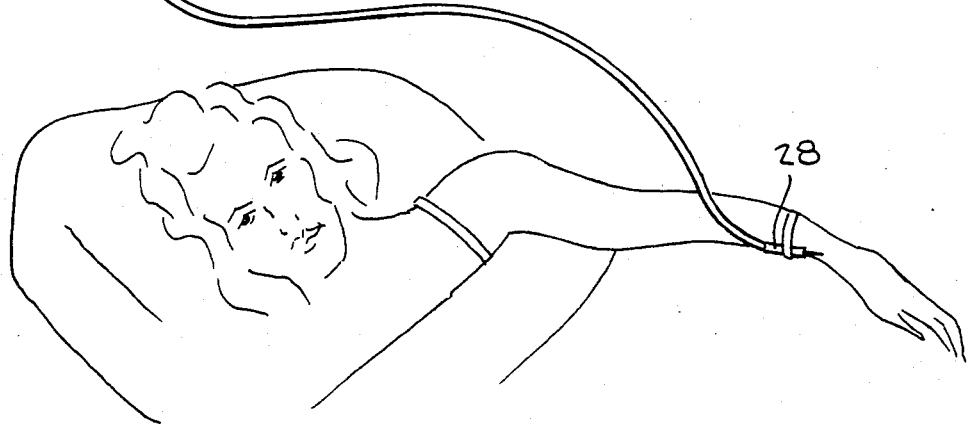
Figures 2, 3:
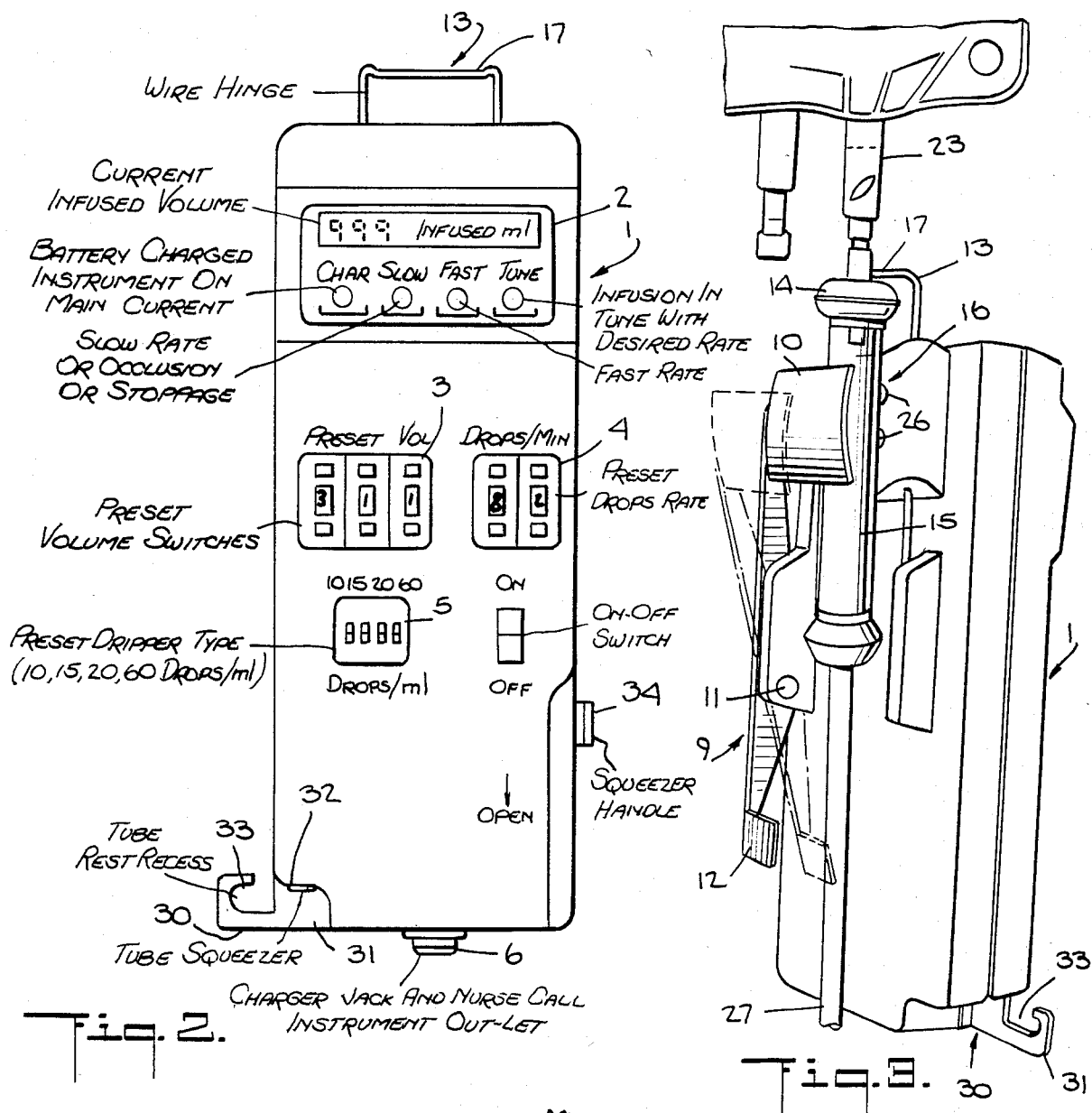
FIG. 2 is a front view of the cartridge of the present invention.
FIG. 3 is a rear view showing the unit in its operative position.
Figure 4:
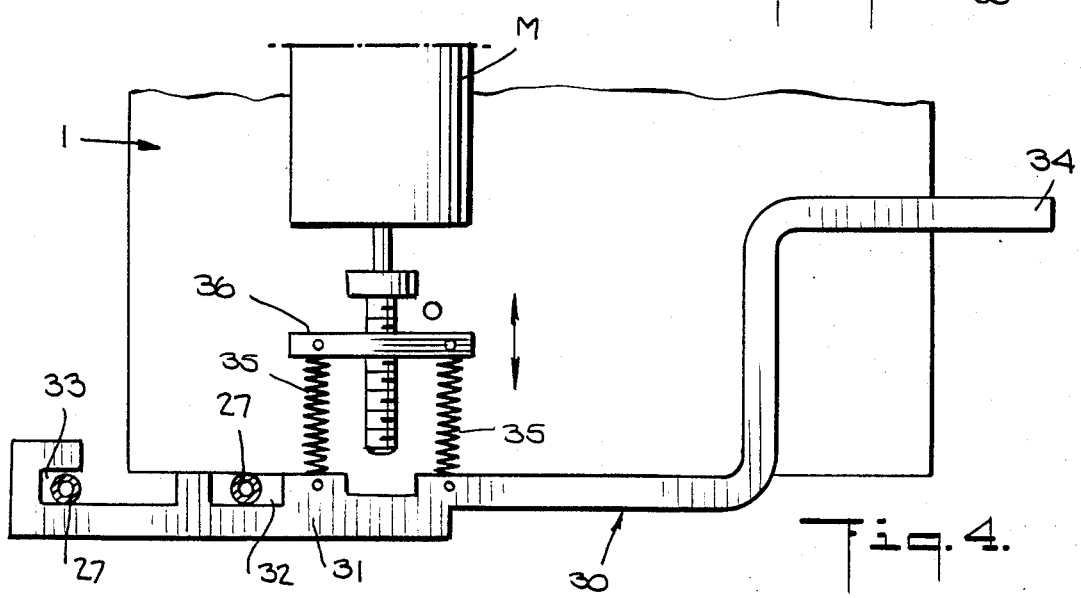
FIG. 4 is a fragmentary plan view showing the automatic tube squeezer mechanism.

Referring more particularly to the drawings and particularly to FIGS. 1 to 4, the improved infusion monitor of the present invention comprises an outer cartridge 1 within which the circuitry and battery is packaged. The infusion liquid is usually stored in a transparent container 20 which may be a rigid or flexible container and may be made of a glass or plastic material. The container 20 is provided with a hanging opening 21 at the top from which it may hang on a hook 22 of an I.V. stand and has an outlet tube 23 at the bottom. Visual measuring indicia 24 may also be provided on the container 20 to give the attendant a visual indication of the amount of fluid remaining therein.

A dripper assembly 15 is inserted in the outlet tube 23. The dripper 15 is provided with an upper flange 14 at its top and is adapted to have a hollow feed tube 27 attached to the bottom thereof. The dripper 15 is a hollow structure preferably made of a transparent plastic or glass material, as is usual in such products. The feeder tube 27 has an intravenous needle 28 attached thereto at its lower end which is adapted to be inserted into the patient for feeding the patient. When the patient is to be infused with a liquid, the attendant sets the cartridge 1 for the rate, volume and type of drip desired (as will be described in greater detail hereinbelow) and the infusion process starts. Display devices 2 are provided in the cartridge 1 to indicate amounts infused as well as to indicate whether the battery is charged and whether the rate of infusion is slow, fast or in tune as will be described in greater detail hereinbelow. The cartridge is also provided with a plurality of switch assemblies 3, 4 and 5 which may be used to pre-set the desired volume, the desired rate and the desired drip-type. The number of drops per CC is pre-set as indicated on the dripper, so that the number of drops counted is translated into infused volume. A charger jack and nurse call instrument outlet 6 may also be provided.

The rear of the cartridge 1 is provided with a clamping assembly in the form of a two-arm lever 9 which is pivotally mounted thereto at pivot 11. The clamping assembly 9 has a clamp 10 at the end of its upper arm and a mirror handle 12, which is used to open and close the clamp 10, at the end of its lower arm. A wire hinge 13 is provided which has an arcuate portion 17 which is adapted to rest on the upper dripper flange 14 of the dripper 15. The dripper tube 15 is adapted to lie in a concave seating surface 16 at the rear of the cartridge 1 and is held in place by the spring-pressed clamp 10. It will be seen from this structure that the cooperation between the wire hinge 13 and the clamp 10 together with the seating surface 16 permits the cartridge 1 to be quickly and easily mounted onto the dripper 15. The flange 14 of the dripper 15 extends above the top edge of the cartridge 1 and the hinge 13 hangs over and rests on the flange 14 so that when the clamp 10 applies pressure to the dripper 15, it will be held tightly within and against the seating surface 16 of the cartridge 1. Hence, the cartridge 1 may be very quickly and easily assembled onto the dripper 15 and may be just as easily disassembled therefrom.

The concave holder 16 is provided with a pair of vertically oriented aligned optical sensing openings 26 which permit sensing beams from the sensing means to pass therethrough. These sensing beams sense the liquid drops as they pass down the dripper tube 15 and are thus able to count the number of drops and determine the rate of infusion. A flexible feed tube 27 leads from the dripper 15 and is adapted to be squeezed to restrict its inner passageway so that the amount of fluid infused is decreased or stopped altogether, and, alternately, the squeezing action of tube 27 may be released to open its inner passageway and allow a greater amount of liquid to be infused.

An automatic squeezing assembly 30 is provided in the cartridge 1 to automatically apply or release pressure on the feed tube 27 to restrict or enlarge its inner passageway. The squeezing assembly 30 comprises an arm 31 having a squeeze notch 32 and rest notch 33 at one end and has a handle 34 at its other end. The arm 30 is connected by a downwardly biased spring 35 to a bracket 36 which is operatively connected to a motor M and which is adapted to raise or lower the squeezing assembly 30. When the motor M is commanded to raise the squeezing assembly 30, the tube 27 is squeezed between the squeeze notch 32 and underside of the cartridge 1 to restrict the passageway of the feed tube 27. When the motor M is commanded to lower the squeezing assembly 30, the pressure on the tube 27 is released so that its passageway is enlarged to permit a greater amount of fluid to be infused. As will be described hereinafter, the motor M may be commanded to squeeze the feed tube 27 to completely stop the flow of liquid. Before the feeding operation is started, the feeding tube 27 is inserted not only in the feeder notch 31 but is also looped around rest notch 33 to prevent the tube 27 from hanging loose and restricting its passageway by its own weight.

Figure 5:
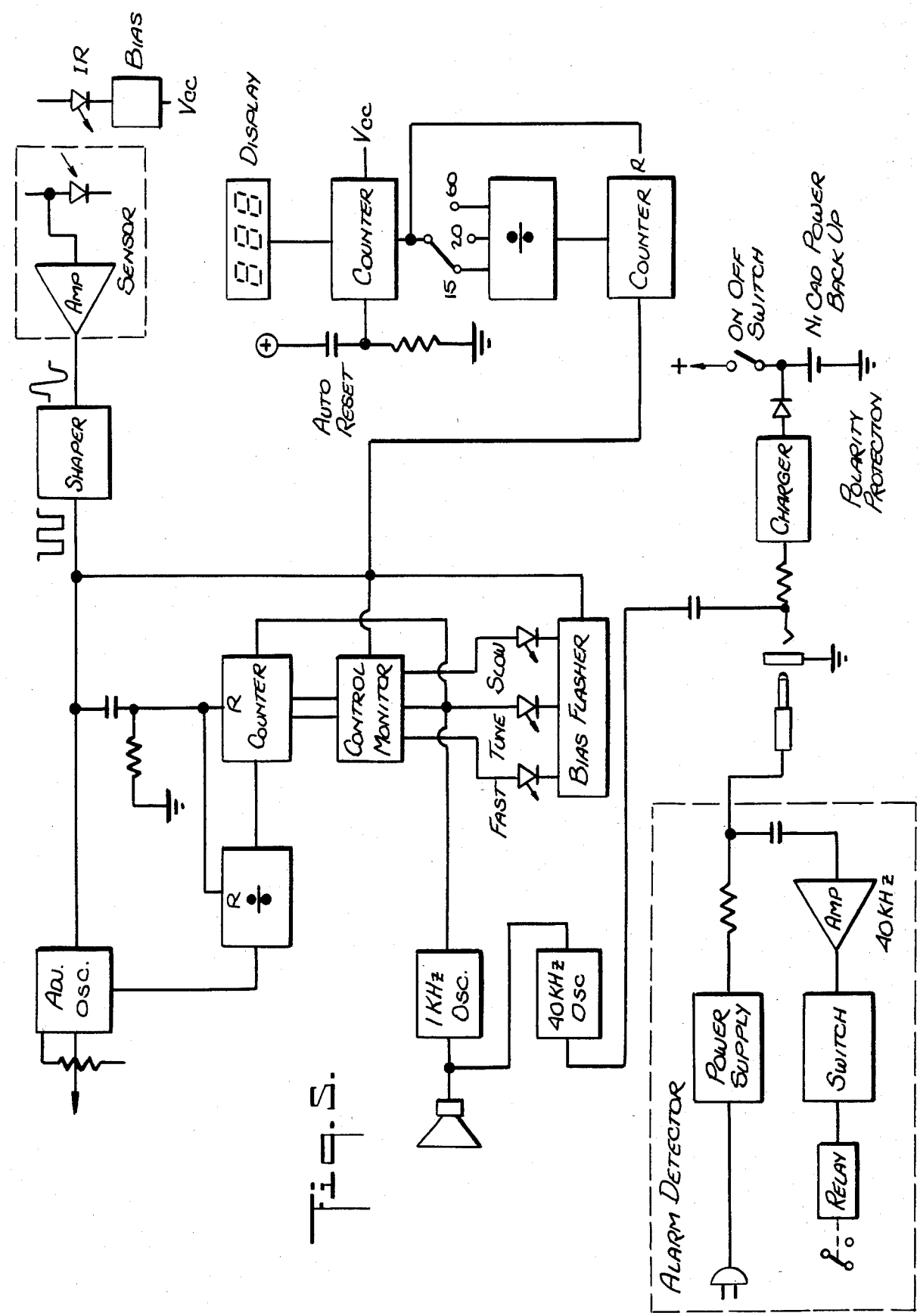
FIG. 5 is a diagrammatic block view showing the circuit used with the present invention.

Referring now to FIGS. 5, 6A, 6B and 7, which show the details of the preferred circuitry used with the present invention. The power source and circuitry is preferably contained entirely within the cartridge 1 so that it can be hung on the dripper. It derives power from a battery (which may have a charger unit) and it comprises diode D1 and transistor Q1 which are paired light emitting diode and photo transistors. The diode D1 is biased on so that the transistor Q1 is also on. When a drop drops through the dripper 15 passes between the diode D1 and the transistor Q1, the drop is sensed through the sensing openings 26 in the cartridge 1. As the drops pass by, the transistor Q1 is momentarily cut-off so that a negative-going pulse is generated. This negative-going pulse is coupled by capacitor C1 into pin 1 of IC1 which is a hex inverter. Five of the six inverters on this chip (4069) are used to shape the pulse into a negative-going square wave.

This negative square wave pulse appears at pin 8 of IC1 and is directly connected to pin 1 of IC3 which is a quad nand-schmidt trigger chip (CD4093). One stage of this chip with its output on pin 3 is used as an oscillator which is activated when the output of pin 8 of IC1 is high and which is cut-off when said pin 8 goes low. Therefore, the duration of an interrupted period of oscillation is the time between successive drops. The frequency of oscillation is controlled by resister R6 which is a front panel activated potentiometer. The frequency of oscillation and the duration will control the number of counts that will be performed by the counter IC2 (CD4520).

The detection system of this invention is formed by IC2 and IC10, together with one section of IC3, and the LED's D4 through D6 which display lights on the front panel. The display lights 6 are marked "slow", "tuned" and "fast". When the drip count is greater than that called for by the setting of potentiometer R6, the "fast" LED lights up. When the drip count corresponds to the number called for by the setting of R6, the "tune" LED lights up. When the drip count is slower than that called for by R6, the "slow" LED is activated.

The stage of IC3 with an output on pin 10 is an 1K oscillator which is activated to drive a speaker when the demanded count is not delivered and constitutes the warning signal. When the dripping stops, the oscillator goes on, and stays on, so that the alarm is constant until an attendant rectifies the situation. The output at pin 10 of IC3 also enables another oscillator whose output is on pin 4 of IC2 and is coupled by C9 to the DC power line. In conjunction with Q2 and RL1 of IC8 it closed switch S3 to enable an alarm in the nurses quarters.

IC4 is a binary counter which counts the number of drops as indicated by the pulse from pin 8 of IC1. The output of IC4 is fed to IC5 which is a dual quad "and" gate, and to a set of three diodes D7 through D9. These diodes are connected to IC6 through a four position switch assembly S2, (S on FIG. 2), a single diode only of which can be accommodated at a time. One position of S2, which is not connected to the diodes, is used to turn on the audible alarm. The other three positions are used to choose which output should be connected to the input of IC6. The outputs of the two "and" gates and the direct output from IC4 are weighted. Each output corresponds to a given number of drips per CC. In this manner, the switch S2 can be set so that the reading on IC8 will indicate total accumulation of CC's delivered and the desired ratio of drops to CC. Likewise, the switches 3 and 4 are comprised of a plurality of sets of diodes and resistors, respectively, as shown in FIG. 7 may be used to pre-set the volume and to pre-set the drop rate. The number of drops per CC is pre-set as indicated on the dripper 15 so that the number of drops counted corresponds to infused volume.

The DC power supply/charge comprises T1, T2 and IC9 and filter capacitor C12. R12, R13 and 21 make up the regulating circuit, keeping the voltage at junction Z1 and D10 to 6.2 V. D10 blocks any reverse current from the battery and also decreases another 0.7 V. The charging current is limited by R12 and R13.

The driving circuit for the motor "M" comprises transistors Q3 through Q6 and diodes D15 through D18 with their associated circuitry. The motor "M" is connected to the "Fast" and "Slow" circuitry of IC10 so that at a command from the "Fast" or "Slow" circuit the motor "M" is activated. The motor "M" is controlled by transistors Q3-Q5 or transistors Q4-Q6. When the "Fast" or "Slow" circuitry of IC10 indicates that the rate is not in tune, i.e. is either faster or slower than the pre-set rate, then the transistor assemblies Q3-Q5 or Q4-Q6 are activated in order to move the motor in one direction or the other so as to squeeze the feed tube 27 to restrict the flow, or to relax the feed tube 27 to increase the flow. This occurs until the amount infused is in tune, at which point there is no pulse from the "Fast"-"Slow" circuitry and the motor stops. As will be understood, if the rate is in tune as pre-set, then there is no pulse and the motor "M" remains inactive. Upon command from the CC measurement circuitry the motor will go its "Maximum squeeze" condition so that after a pre-set number of CC's have been delivered to the patient, flow is stopped entirely.

It will thus be seen that the present invention provides an improved infusion monitor which may be easily hung from the dripper which will automatically and continuously monitor and adjust the desired flow rate, which will continuously indicate the amount of fluid infused into the patient, which may be pre-set to control the flow infused or shut-off the flow when the desired volume has been administered, and which is provided with warning devices which give signals at the patient's side and/or at the nurse's desk so that the attendant is alerted to any variation or stoppage of the pre-set infusion rate.

Although the present invention has been described with respect to an infusion monitor for feeding liquids to patients for medical purposes, it will be understood that this system may be used for monitoring the infusion of liquids for purposes other than medical purposes.

As many and varied modifications of the subject matter of this invention will become apparent to those skilled in the art from the detailed description given hereinabove, it will be understood that the present invention is limited only as provided in the claims appended hereto.

The embodiments of the invention in which an exclusive property or privilege is claimed are defined as follows:

1. A liquid infusion monitor system comprising a reservoir for liquid, an infusion tube assembly operatively associated with said reservoir and including an infusion tube, a single cartridge mounted adjacent the infusion tube assembly with one side of the cartridge facing said infusion tube assembly for monitoring the amount of liquid passing through said infusion tube assembly, said cartridge having contained therein: (a) means for pre-setting the amount of liquid, (b) means for sensing the amount of fluid passing through said infusion tube assembly and (c) means for automatically increasing or decreasing the amount of liquid infused to conform to said pre-set amounts, said sensing means comprising a pair of sensing openings located on said side of said cartridge facing the infusion tube assembly, reflecting means opposite said sensing openings, said sensing means comprising means for emitting a sensing beam through one of said sensing openings toward said reflecting means and means for receiving said sensing beam through the other of said sensing openings after said sensing beam is reflected from said reflecting means, a seating surface in a wall on said cartridge, said seating surface having an open face which faces outwardly from the said cartridge and away from said wall and adapted to receive the infusion tube assembly, said sensing opening being centrally located at the base of said seating surface, said seating surface being shaped to automatically locate said infusion tube assembly within the seating surface whereby the said infusion tube assembly will automatically be properly located with respect to said sensing openings.

2. An infusion monitor system as claimed in claim 1, wherein said cartridge having a squeezing assembly extending from an outside wall thereof, an infusion tube being mounted between said squeezing assembly and said outside wall and wherein means are provided in the cartridge for moving the squeezing assembly in one direction to apply pressure to the infusion tube to squeeze it against said outside wall and for moving the squeezing assembly in the opposite direction to release pressure on the infusion tube.

3. An infusion monitor system as claimed in claim 2, wherein said squeezing assembly comprises a squeeze notch adapted to receive the infusion tube and wherein movement in one direction will release pressure on the tube and movement in the opposite direction will apply pressure on the tube to squeeze it.

4. An infusion monitor system as claimed in claim 3, wherein motor means are provided in the cartridge to move the squeeze assembly in either direction.

5. An infusion monitor system as claimed in claim 4, wherein spring connection means are provided between the squeeze assembly and said motor means.

6. An infusion monitor system as claimed in claim 5, wherein a manually operable squeezer handle means are provided to move the squeezing assembly and permit an infusion tube to be mounted in its notch.

7. An infusion monitor system as claimed in claim 6, wherein said squeezer assembly is provided with a rest notch in which the infusion tube is mounted.

8. An infusion monitor system as claimed in claim 7, wherein a dripper assembly is interposed between said reservoir and said infusion tube and wherein said cartridge is removably mounted on said dripper assembly.

9. An infusion monitor system as claimed in claim 8, wherein sensing beams are directed at the dripper through said openings in order to sense the liquid drips passing through the dripper assembly.

10. An infusion monitor system as claimed in claim 9, wherein a wire hinge is provided on the cartridge and is adapted to rest on the dripper assembly.

11. An infusion monitor system as claimed in claim 10, wherein said cartridge is provided with a dripper-receiving surface in which the dripper assembly rests and wherein clamp means are provided on the cartridge to cooperate with said wire hinge to hold the cartridge on the dripper assembly.

12. An infusion monitor system as claimed in claim 11, wherein said clamping assembly comprises a two arm lever having a clamping means on one end adapted to apply pressure to the dripper assembly and hold it in the said seating surface.

13. An infusion monitor system as claimed in claim 12, wherein a handle is provided on the other end of the two arm lever to permit the clamping means to move away from the dripper assembly to release the dripper assembly from the cartridge.

14. An infusion monitor system as claimed in claim 13, wherein said seating surface is a concave seating surface and wherein said openings are in said seating surface.

15. An infusion monitor system as claimed in claim 14, wherein said sensing means are comprised of a pair of light emitting diode and photo transistors.

16. An infusion monitor system as claimed in claim 15, wherein said diode is biased on so that the transistor is on.

17. An infusion monitor system as claimed in claim 16, wherein passage of a drop of liquid through the dripper is sensed by said diode and transistor to momentarily interrupt the transistor to form a negative-going pulse.

18. An infusion monitor system as claimed in claim 17, wherein said negative-going pulse is coupled with a hex inverter by a capacitor and wherein said negative-going pulse is shaped into a square wave.

19. An infusion monitor system as claimed in claim 18, wherein said negative square wave is connected to a quad nand-schmidt trigger, one stage of which acts as an oscillator adapted to be activated when the output is high and interrupted when the output is low whereby the duration of an interrupted period of oscillation is the time between successive drops.

20. An infusion monitor system as claimed in claim 19, wherein the frequency of oscillation is controlled by a potentiometer which may be pre-set, whereby the frequency of oscillation and the duration controls the number of counts that will be performed by a counter.

21. An infusion monitor system as claimed in claim 20, wherein a detection system is provided with a plurality of LEDs, which display through infusion monitor assembly, light to indicate that the drip count is slow, tuned or fast whereby when the drip count is greater than said pre-set potentiometer setting the fast LED is activated, when the drip count corresponds to said pre-set potentiometer setting the tune LED is activated and when the drip count is slower than said pre-set potentiometer setting the slow LED is activated.

22. An infusion monitor system as claimed in claim 21, wherein means are provided for activating a warning signal when the pre-set amount is not delivered.

23. An infusion monitor system as claimed in claim 22, wherein said motor means are operatively connected to the fast and slow circuitry so that the circuitry commands the motor to be activated.

24. An infusion monitor system as claimed in claim 23, wherein said motor means comprises transistor assemblies for controlling its function.

25. An infusion monitor system as claimed in claim 24, wherein said transistor assemblies command the motor to move in one direction or the other to either increase or decrease the amount of fluid infused and wherein said movement will continue until the amount infused is in tune at which point no pulse is emitted from the fast-slow circuitry and the motor stops.

26. An infusion monitor system as claimed in claim 25, wherein after a pre-set number of CCs have been delivered, the motor will move to maximum squeeze condition to stop the flow of liquid.

27. An infusion monitor system as claimed in claim 26, wherein said warning signal comprises an oscillator to sound an alarm.

28. An infusion monitor system as claimed in claim 27, wherein switch means are provided to indicate total accumulation delivered and predetermined drop ratio to-CC as well as volume and drop rate.

29. An infusion monitor system as claimed in claim 28, wherein said switch means comprise diode and resistor means.

30. A cartridge for use with a liquid infusion monitor system having an infusion tube assembly for monitoring the amount of liquid infused through the infusion tube assembly and being adapted to be mounted adjacent the infusion tube assembly with one side thereof facing the infusion tube assembly, said cartridge having contained therein (a) means for pre-setting the amount of liquid infused, (b) means for sensing the amount of liquid passing through the infusion tube assembly and (c) means for automatically increasing or decreasing the amount of liquid infused to conform to said pre-set amounts said sensing means comprising a pair of sensing openings located on said side of said cartridge facing the infusion tube assembly, reflecting means opposite said sensing openings, said sensing means comprising means for emitting a sensing beam through one of said sensing openings toward said reflecting means and means for receiving said sensing beam through the other of said sensing openings after said sensing beam is reflected from said reflecting means, a seating surface in a wall on said cartridge, said seating surface having an open face which faces outwardly from the said cartridge and away from said wall and adapted to receive the infusion tube assembly, said sensing opening being centrally located at the base of said seating surface, said seating surface being shaped to automatically locate said infusion tube assembly within the seating surface whereby the said infusion tube assembly will automatically be properly located with respect to said sensing openings.

31. A cartridge as claimed in claim 30, wherein said automatic means comprises a squeezing assembly extending from an outside wall thereof, an infusion tube being mounted between said squeezing assembly and said outside wall and wherein means are provided for moving the squeezing assembly in one direction to apply pressure to an infusion tube to squeeze it against said outside wall and for moving the squeezing assembly in the opposite direction to release pressure on an infusion tube.

32. A cartridge as claimed in claim 30, wherein said squeezing assembly comprises a squeeze notch adapted to receive the infusion tube and wherein movement in one direction will release pressure on an infusion tube and movement in the opposite direction will apply pressure on an infusion tube and to squeeze it.

33. A cartridge as claimed in claim 32, wherein motor means are provided to move the squeeze assembly in either direction.

34. A cartridge as claimed in claim 33, wherein spring connection means are provided between the squeeze assembly and said motor means.

35. A cartridge as claimed in claim 34, wherein a manually operable squeezer handle means are provided to move the squeezing assembly and permit an infusion tube to be mounted in its notch.

36. A cartridge as claimed in claim 35, wherein said squeezer assembly is provided with a rest notch in which the infusion tube is mounted.

37. A cartridge as claimed in claim 36, wherein a pair of sensing openings are provided in the infusion monitor assembly through which sensing beams are emitted in order to sense the liquid drips being infused.

38. A cartridge as claimed in claim 37, wherein a wire hinge is provided on the infusion monitor assembly.

39. A cartridge as claimed in claim 38, wherein a dripper assembly receiving surface is provided and clamp means are provided to cooperate with said wire hinge to hold the infusion monitor assembly in its monitoring position.

40. A cartridge as claimed in claim 39, wherein said clamping assembly comprises a two arm lever having a clamping means on one end adapted to apply pressure to a dripper assembly.

41. A cartridge as claimed in claim 40, wherein a handle is provided on the other end of the two arm lever to permit the clamping means to move away from a dripper assembly.

42. A cartridge as claimed in claim 41, wherein said seating surface is a concave seating surface and wherein said openings are in said seating surface.

43. A cartridge as claimed in claim 42, wherein said sensing means are comprised of a pair of light emitting diode and photo transistors.

44. A cartridge as claimed in claim 43, wherein said diode is biased on so that the transistor is on.

45. A cartridge as claimed in claim 44, wherein passage of a drop of liquid through the dripper is sensed by said diode and transistor to momentarily interrupt the transistor to form a negative-going pulse.

46. A cartridge as claimed in claim 45, wherein said negative-going pulse is coupled with a hex inverter by a capacitor and wherein said negative-going pulse is shaped into a square wave.

47. A cartridge as claimed in claim 46, wherein said negative square wave is connected to a quad nand-schmidt trigger, one stage of which acts as an oscillator adapted to be activated when the output is high and interrupted when the output is low whereby the duration of an interrupted period of oscillation is the time between successive drops.

48. A cartridge as claimed in claim 47, wherein the frequency of oscillation is controlled by a potentiometer which may be pre-set, whereby the frequency of oscillation and the duration controls the number of counts that will be performed by a counter.

49. A cartridge as claimed in claim 48, wherein a detection system is provided with a plurality of LEDs, which display through infusion monitor assembly, light to indicate that the drip count is slow, tuned or fast whereby when the drip count is greater than said pre-set potentiometer setting the fast LED is activated, when the drip count corresponds to said pre-set potentiometer setting the tune LED is activated and when the drip count is slower than said pre-set potentiometer setting the slow LED is activated.

50. A cartridge as claimed in claim 49, wherein means are provided for activating a warning signal when the pre-set amount is not delivered.

51. A cartridge as claimed in claim 50, wherein said motor means are operatively connected to the fast and slow circuitry so that the circuitry commands the motor to be activated.

52. A cartridge as claimed in claim 51, wherein said motor means comprises transistor assemblies for controlling its function.

53. A cartridge as claimed in claim 52, wherein said transistor assemblies command the motor to move in one direction or the other to either increase or decrease the amount of fluid infused and wherein said movement will continue until the amount infused is in tune at which point no pulse is emitted from the fast-slow circuitry and the motor stops.

54. A cartridge as claimed in claim 53, wherein after a pre-set number of CCs have been delivered, the motor will move to maximum squeeze condition to stop the flow of liquid.

55. A cartridge as claimed in claim 54, wherein said warning signal comprises an oscillator to sound an alarm.

56. A cartridge as claimed in claim 55, wherein switch means are provided to indicate total accumulation delivered and predetermined drop ratio to-CC as well as volume and drop rate.

57. A cartridge as claimed in claim 56, wherein said switch means comprise diode and resistor means.

58. A liquid infusion monitor assembly comprising a cartridge, means within the cartridge for pre-setting the amount of liquid infused, means within the cartridge for pre-setting the number of drops per cubic centimeter, means within the cartridge for monitoring the amount of liquid infused, means within the cartridge for automatically increasing or decreasing the amount of liquid infused to conform to said pre-set amounts, a pair of sensing openings in said cartridge through which sensing beams are emitted in order to sense the liquid drips being infused, means on the cartridge for removably mounting the cartridge on one side of an infusion conduit, the circuit components for the pre-setting, monitoring and automatic means being mounted entirely within said cartridge, said sensing openings being on the same side of said cartridge, said mounting means comprising a wire hinge on the cartridge, a dripper assembly-receiving surface is provided in the cartridge, clamp means are provided on the cartridge to cooperate with said wire hinbge to hold the cartridge in its monitoring position, said clamping means comprises a two arm lever having a clamping means on one end adapted to apply pressure to a dripper assembly, a mirror handle on the other end of the two arm lever to permit the clamping means to move away from a dripper assembly, said receiving surface is a concave seating surface and said sensing openings are in said receiving surface, said sensing means are comprised of a pair of light emitting diode and photo transistors, said diode being biased on so that the transistor is on, whereby passage of a drop of liquid through the dripper is sensed by said diode and transistor to momentarily interrupt the transistor to form a negative-going pulse, said negative-going pulse being coupled with a hex inverter by a capacitor and wherein said negative-going pulse is shaped into a square wave.

59. An infusion monitor assembly as claimed in claim 58, wherein said negative square wave is connected to a quad nand-schmidt trigger, one stage of which acts as an oscillator adapted to be activated when the output is high and interrupted when the output is low whereby the duration of an interrupted period of oscillation is the time between successive drops.

60. An infusion monitor assembly as claimed in claim 59, wherein the frequency of oscillation is controlled by a potentiometer which may be pre-set, whereby the frequency of oscillation and the duration controls the number of counts that will be performed by a counter.

61. An infusion monitor assembly as claimed in claim 60, wherein a detection system is provided with a plurality of LEDs, which display through infusion monitor assembly, light to indicate that the drip count is slow, tuned or fast whereby when the drip count is greater than said pre-set potentiometer setting the fast LED is activated, when the drip count corresponds to said pre-set potentiometer setting the tune LED is activated and when the drip count is slower than said pre-set potentiometer setting the slow LED is activated.

62. An infusion monitor assembly as claimed in claim 61, wherein means are provided for activating a warning signal when the pre-set amount is not delivered.

63. An infusion monitor assembly as claimed in claim 62, wherein said motor means are operatively connected to the fast and slow circuitry so that the circuitry commands the motor to be activated.

64. An infusion monitor assembly as claimed in claim 63, wherein said motor means comprises transistor assemblies for controlling its function.

65. An infusion monitor assembly as claimed in claim 64, wherein said transistor assemblies command the motor to move in one direction or the other to either increase or decrease the amount of liquid infused and wherein said movement will continue until the amount infused is in tune at which point no pulse is emitted from the fast-slow circuitry and the motor stops.

66. An infusion monitor assembly as claimed in claim 65, wherein after a pre-set number of CCs have been delivered, the motor will move to maximum squeeze condition to stop the flow of liquid.

67. An infusion monitor assembly as claimed in claim 66, wherein said warning signal comprises an oscillator to sound an alarm.

68. An infusion monitor assembly as claimed in claim 67, wherein switch means are provided to indicate tool accumulation delivered and predetermined drop ratio to-CC as well as volume and drop rate.

69. An infusion monitor assembly as claimed in claim 68, wherein said switch means comprise diode and resistor means.

70. A liquid infusion monitor assembly comprising a cartridge, means within the cartridge for pre-setting the amount of liquid infused, means within the cartridge for pre-setting the number of drops per cubic centimeter, means within the cartridge for monitoring the amount of liquid infused, means within the cartridge for automatically increasing or decreasing the amount of liquid infused to conform to said pre-set amounts, means on the cartridge for removably mounting the cartridge on one side of an infusion conduit, the circuit components for the pre-setting, monitoring and automatic means being mounted entirely within said cartridge, a pair of sensing openings being provided in the carriage through which sensing beams are emitted in order to sense the liquid drips being infused, said sensing openings being on the same side of said cartridge, said sensing means comprised of a pair of light emitting diode and photo transistors, said diode being biased on so that the transistor is on whereby passage of a drop of liquid through the dripper is sensed by said diode and transistor to momentarily interrupt the transistor to form a negative-going pulse, said negative-going pulse being coupled with a hex inverter by a capacitor and wherein said negative-going pulse is shaped into a square wave.

71. An infusion monitor assembly as claimed in claim 70, wherein said negative square wave is connected to a quad nand-schmidt trigger, one stage of which acts as an oscillator adapted to be activated when the output is high and interrupted when the output is low whereby the duration of an interrupted period of oscillation is the time between successive drops.

72. An infusion monitor assembly as claimed in clam 71, wherein the frequency of oscillation is controlled by a potentiometer which may be pre-set, whereby the frequency of oscillation and the duration controls the number of counts that will be performed by a counter.

73. An infusion monitor assembly as claimed in claim 72, wherein a detection system is provided with a plurality of LEDs, which display through infusion monitor assembly, light to indicate that the drip count is slow, tuned or fast whereby when the drip count is greater than said pre-set potentiometer setting the fast LED is activated, when the drip count corresponds to said pre-set potentiometer setting the tune LED is activated and when the drip count is slower than said pre-set potentiometer setting the slow LED is activated.

74. An infusion monitor assembly as claimed in claim 73, wherein means are provided for activating a warning signal when the pre-set amount is not delivered.

75. An infusion monitor assembly as claimed in claim 74, wherein said motor means are operatively connected to the fast and slow circuitry so that the circuit commands the motor to be activated.

76. An infusion monitor assembly as claimed in claim 75, wherein said motor means comprises transistor assemblies for controlling its function.

77. An infusion monitor assembly as claimed in claim 76, wherein said transistor assemblies command the motor to move in one direction or the other to either increase or decrease the amount of fluid infused and wherein said movement will continue until the amount infused is in tune at which point no pulse is emitted from the fast-slow circuitry and the motor stops.

78. An infusion monitor assembly as claimed in claim 77, wherein after a pre-set number of CCs have been delivered, the motor will move to maximum squeeze condition to stop the flow of liquid.

79. An infusion monitor assembly as claimed in claim 78, wherein said warning signal comprises an oscillator to sound an alarm.

80. An infusion monitor assembly as claimed in claim 79, wherein switch means are provided to indicate total accumulation delivered and predetermined drop ratio to-CC as well as volume and drop rate.

81. An infusion monitor assembly as claimed in claim 80, wherein said switch means comprise diode and resistor means.

* * * * *